United States Patent
Will

(10) Patent No.: US 10,752,891 B2
(45) Date of Patent: Aug. 25, 2020

(54) PROTEIN-BASED SAMPLE COLLECTION MATRICES AND DEVICES

(71) Applicant: Roche Molecular Systems, Inc., Pleasanton, CA (US)

(72) Inventor: Stephen Will, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 146 days.

(21) Appl. No.: 15/592,481

(22) Filed: May 11, 2017

(65) Prior Publication Data
US 2017/0327815 A1    Nov. 16, 2017

Related U.S. Application Data

(60) Provisional application No. 62/336,342, filed on May 13, 2016.

(51) Int. Cl.
| | | |
|---|---|---|
| *C12N 15/10* | (2006.01) | |
| *C12Q 1/6806* | (2018.01) | |
| *G01N 1/10* | (2006.01) | |
| *A61B 10/02* | (2006.01) | |
| *G01N 1/02* | (2006.01) | |

(52) U.S. Cl.
CPC ..... *C12N 15/1006* (2013.01); *C12N 15/1013* (2013.01); *C12Q 1/6806* (2013.01); *G01N 1/10* (2013.01); *A61B 10/02* (2013.01); *A61B 2010/0216* (2013.01); *G01N 2001/028* (2013.01)

(58) Field of Classification Search
CPC ...... G01N 2001/028; A61B 2010/0216; A61B 10/02; C12Q 1/6806; C12N 15/1013; C12N 15/1006
See application file for complete search history.

(56) References Cited

U.S. PATENT DOCUMENTS

| | | | |
|---|---|---|---|
| 2004/0009496 A1* | 1/2004 | Eiblmaier | C07H 21/04 435/6.12 |
| 2014/0017676 A1* | 1/2014 | Morhet | C12N 15/1006 435/6.11 |

FOREIGN PATENT DOCUMENTS

| | | |
|---|---|---|
| WO | 1999061454 | 12/1999 |

OTHER PUBLICATIONS

Awny, Mona M. et al. "Storing DNA on fabric." Forensic Magazine (2011) accessed by the examiner on Feb. 19, 2019 at <http://https://www.forensicmag.com/article/2011/04/storing-dna-fabric>. (Year: 2011).*
Huh et al. (1967) Analytical Biochemistry 19:150.
Ellem (1966) J. Molecular Biology 20:283.
Holoubek (1967) Analytical Biochemistry 18:375.
Boom et al. (1999) J. Clinical Microbiology 37:615.
Kluge, J.A. et al., Silk-based blood stabilization for diagnostics, PNAS, Apr. 5, 2016.

* cited by examiner

*Primary Examiner* — Christopher Adam Hixson
(74) *Attorney, Agent, or Firm* — Eric Grant Lee; Carol Johns

(57) ABSTRACT

Provided herein are methods and compositions to effectively isolate nucleic acids using protein-based sample collection matrices.

13 Claims, 4 Drawing Sheets

PROTEIN-BASED SAMPLE COLLECTION MATRICES AND DEVICES

BACKGROUND OF THE INVENTION

The recovery of nucleic acids from a solid or semi-solid collection matrix is widely accepted in molecular diagnostics. Typical examples of matrices include swabs and paper substrates. Recovery of nucleic acids from these materials can be challenging because of inefficient extraction from the substrate material and potential interference from the material with pipetting or other liquid handling devices. In addition, the presence of a solid substance in an instrument can trigger an Error signal, resulting in an aborted extraction or other delay.

Efficiency of recovery of nucleic acids can be enhanced by use of harsh and/or toxic conditions such as phenol/chloroform, and indeed this has been attempted with polymeric swabs. Existing solid substrates, however, are not soluble in guanidinium and other milder chaotropic solutions.

SUMMARY OF THE INVENTION

Provided herein is a protein-based sample collection matrix that allows for efficient nucleic acid recovery, compatibility with instrumentation, and use of chaotropic buffers (e.g., guanidinium-based).

Provided herein are methods and compositions for collecting nucleic acids from a biological sample. In some embodiments, a kit is provided comprising a) a protein-based matrix configured to collect sample; and b) a solution comprising about 3-6 M chaotrope, about 0.5-10% detergent, about 50-500 mM reducing agent, and buffer maintaining the pH of the solution at about 5-8. In some embodiments, the protein-based matrix forms a swab. In some embodiments, the protein-based matrix forms a strip to collect a liquid sample (e.g., blood, blood component, urine, saliva, mucus, etc.). In some embodiments, the protein-based matrix is moistened and used as a wipe to collect sample from a surface (e.g., in a hospital or forensic context, or on skin).

In some embodiments, the kit further comprises processing vessels, e.g., for solubilizing the sample-bound, protein-based matrix. In some embodiments, the kit further comprises filter tubes, magnetic glass beads (MGPs), or other components for separating the analyte of interest (e.g., nucleic acids). In some embodiments, the kit further includes wash buffer (or stock solution or dry wash buffer components to rehydrate). In some embodiments, the kit further includes elution buffer (or stock solution or dry elution buffer components to rehydrate). In some embodiments, the kit further includes proteinase, e.g., proteinase K. In some embodiments, the kit further includes a container for storing the sample-bound, protein-based matrix.

In some embodiments, the protein-based matrix includes silk, e.g., silk fabric. In some embodiments, the protein-based matrix is modified, e.g., to increase affinity for the analyte, e.g., with positively charged moieties to bind nucleic acids.

In some embodiments, the chaotrope is a guanidinium salt or combination of guanidinium salts. In some embodiments, the detergent is a non-ionic detergent, e.g., polydocanol or Tween. In some embodiments, the reducing agent is DTT or beta-mercaptoethanol. In some embodiments, the buffer is a citrate buffer. In some embodiments, the pH of the solution is 5.8-7, e.g., 6-6.8.

Further provided are methods for collecting nucleic acids in a sample, the method comprising contacting the sample containing nucleic acids on a protein-based matrix, thereby collecting the analyte. In some embodiments, the method further includes placing the sample-bound, protein-based matrix in a container for storage. In some embodiments, the protein-based matrix includes silk. In some embodiments, the protein-based matrix is modified, e.g., to increase affinity for the analyte, e.g., with positively charged moieties to bind nucleic acids or with antibody moieties to bind specific protein targets.

In some embodiments, the method further includes contacting the protein-based matrix with a solution comprising about 3-6 M chaotrope, about 0.5-10% detergent, about 50-500 mM reducing agent, and buffer maintaining pH of the solution at about 5-8, thereby solubilizing the protein-based matrix in the solution. In some embodiments, the protein-based matrix is immersed in the solution for at least 5 minutes, e.g., 10-180 minutes, 20-60 minutes, etc. In some embodiments, the solution and protein-based matrix are heated, e.g., to 30-60 C, to speed dissolution of the matrix. In some embodiments, the chaotrope is a guanidinium salt or combination of guanidinium salts. In some embodiments, the detergent is a non-ionic detergent, e.g., polydocanol or Tween. In some embodiments, the reducing agent is DTT or beta-mercaptoethanol. In some embodiments, the buffer is a citrate buffer. In some embodiments, the pH of the solution is 5.8-7, e.g., 6-6.8.

In some embodiments, the method further includes contacting the solution with a filter tube or with magnetic glass beads (MGPs), washing the filter tube or MGPs with wash buffer, and eluting the nucleic acids from the filter tube or MGPs with elution buffer, thereby isolating the nucleic acids from the sample. In some embodiments, the sample is a liquid sample, e.g., blood, blood component, urine, saliva, mucus, etc. In some embodiments, the protein-based matrix is moistened and used as a wipe to collect sample from a surface (e.g., in a hospital or forensic context, or on skin).

DETAILED DESCRIPTION OF THE INVENTION

I. Introduction

Figure 1:
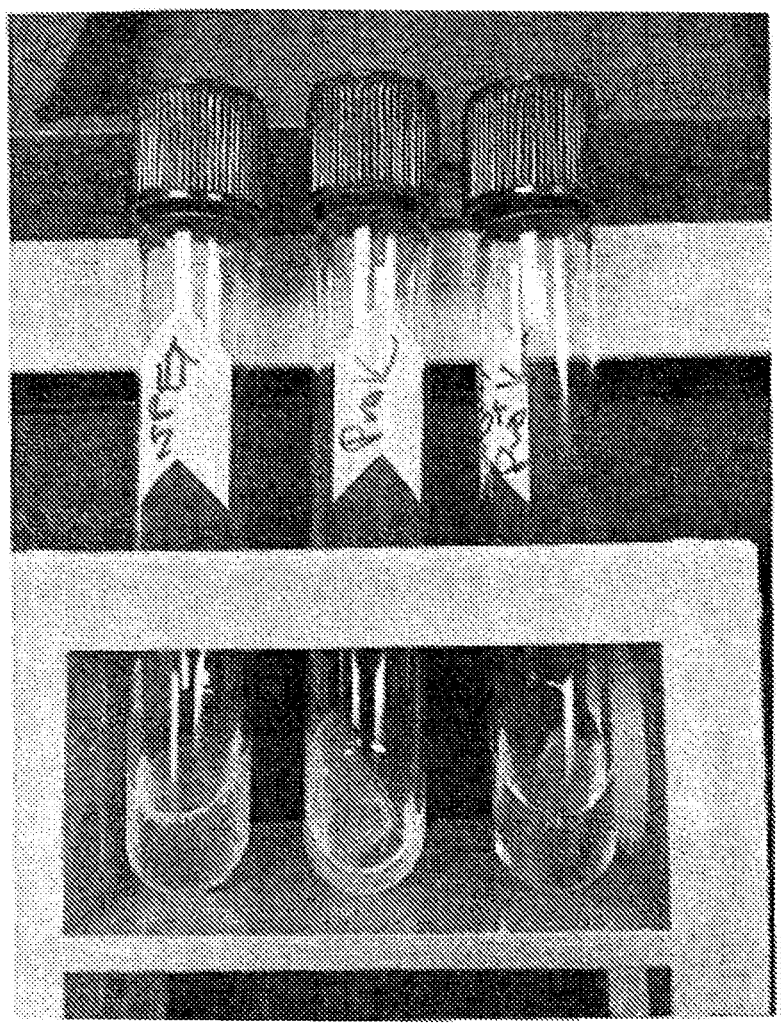
FIG. 1 shows three tubes, each containing a protein-based matrix strip (silk) in a different solution.

Provided herein is a protein-based sample collection matrix that allows for efficient nucleic acid recovery, compatibility with instrumentation, and use of chaotropic solutions (e.g., guanidinium-based). The protein-based matrix can be used to collect samples and bind nucleic acids in the sample. The nucleic acids need not be eluted or otherwise removed from the matrix, because the protein-based matrix dissolves in chaotropic solution. This results in efficient nucleic acid recovery. The dissolved (solubilized) protein also will not interfere with pipetting or detection instrumentation. The matrix can also be conveniently formed into a variety of shapes depending on the intended use. For example, a strip can be used to collect liquid samples (e.g., blood or saliva droplets), a swab can be used to collect cellular samples (e.g., buccal or cervical), or a wipe can be used to test surfaces for the presence of microbes or nucleic acids from any source (e.g., in a hospital or forensic setting).

The protein-based matrix can be used as an initial nucleic acid capture step and combined with additional nucleic acid purification steps, e.g., using solid supports. Alternatively, the solubilized nucleic acid-protein solution can be used directly in detection assays.

II. Definitions

The term "protein-based matrix" or "protein-based substrate" refers to a substance that is composed primarily of protein that can be used to capture components of a biological sample, including nucleic acids, proteins, etc. in the sample, while remaining insoluble in water and physiological liquids. The protein-based matrix can, however, be solubilized (degraded or dispersed) in chaotropic conditions as described herein. Proteins that can be used in a protein-based matrix include those that remain insoluble in water and physiological sample conditions, and ideally can be formed into multiple formats (flat strip, well, array location, fibrous swab or wipe), and are well-tolerated on contact with skin or mucosal membranes. Examples include but are not limited to silk, keratin, collagen, albumin, milk proteins, and combinations of any number thereof. Non-protein components of a protein-based matrix can include materials that improve adsorption, specific targeting, or stabilization of the desired analytes or to improve the mechanical properties of the matrix.

The term "solid (or semisolid) support" is used herein to denote an inert surface or body to which an agent, such as nucleic acid can be immobilized. Non-limiting examples include glass, silica, plastic, nitrocellulose, membranes, chips, and particles (e.g., magnetic glass particles or MGPs).

The term "in solution," e.g., referring to a solid support in solution, can indicate that the solid support is exposed to a solution (e.g., in contact with reagents in solution) or that the solid supports themselves are in solution (e.g., beads or particles suspended in liquid). The term is used to distinguish a situation where a matrix is actually solubilized, dissolved, or degraded in a liquid, and a situation where particles remain intact but suspended in solution.

The terms "receptacle," "vessel," "tube," "well," "chamber," "microchamber," etc. refer to a container that can hold dry and/or liquid components, a matrix, reagents or an assay. If the receptacle is in a kit and holds matrix carrying sample, reagents, or an amplification reaction, it can be closed or sealed to avoid contamination or evaporation. If the receptacle is being used for an assay, it can be open or accessible, at least during set up of the assay.

The term "immobilize," "immobilizing," "capture," "capturing," "bind," or "binding," in the context of a matrix or solid support binding nucleic acid, refers to non-covalent binding. Immobilization can include absorption, where the sample is retained within the voids in the protein-based matrix, and/or adsorption, where sample components attracted to the surface of the protein-based matrix. Sample typically dries or is captured on a protein-based matrix described herein so that nucleic acids adhere to the matrix. Native proteins suitable for the construction of a protein-based matrix may have limited affinity for the analyte of interest, so the native protein can be linked to or blended with a different protein or polypeptide sequence that has higher affinity (e.g., positively charged amino acids to attract negatively charged nucleic acids). Such blended proteins can be produced recombinantly, or modified by partial hydrolysis to alter the isoelectric point. A protein can also be modified by introducing a structural or chemical moiety to increase retention of the desired analyte. Modifications include antibodies, haptens, and thiol, amine, and carboxylic acid moieties.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophore-labeled nucleotides.

The term "primer" refers to a short nucleic acid (an oligonucleotide) that acts as a point of initiation of polynucleotide strand synthesis by a nucleic acid polymerase under suitable conditions. Polynucleotide synthesis and amplification reactions typically include an appropriate buffer, dNTPs and/or rNTPs, and one or more optional cofactors, and are carried out at a suitable temperature. A primer typically includes at least one target-hybridized region that is at least substantially complementary to the target sequence (e.g., having 0, 1, 2, or 3 mismatches). This region of is typically about 8 to about 40 nucleotides in length, e.g., 12-25 nucleotides. The term "probe" refers any molecule that is capable of selectively binding to a specifically intended target biomolecule. For example, a probe can be a nucleic acid having complimentary sequence to a nucleic acid sequence of interest.

The words "complementary" or "complementarity" refer to the ability of a nucleic acid in a polynucleotide to form a base pair with another nucleic acid in a second polynucleotide. For example, the sequence A-G-T (A-G-U for RNA) is complementary to the sequence T-C-A (U-C-A for RNA). Complementarity may be partial, in which only some of the nucleic acids match according to base pairing, or complete, where all the nucleic acids match according to base pairing. A probe or primer is considered "specific for" a target sequence if it is at least partially complementary to the target sequence. Depending on the conditions, the degree of complementarity to the target sequence is typically higher for a shorter nucleic acid such as a primer (e.g., greater than 80%, 90%, 95%, or higher) than for a longer sequence.

The terms "identical" or "percent identity," in the context of two or more nucleic acids, or two or more polypeptides, refer to two or more sequences or subsequences that are the same or have a specified percentage of nucleotides, or amino acids, that are the same (e.g., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an a sequence that is at least about 8-25 amino acids or nucleotides in length, or over a region that is 50-100 amino acids or nucleotides in length, or over the entire length of the reference sequence.

The term "kit" refers to any manufacture (e.g., a package or a container) including at least one reagent, such as a solution or buffer for capturing, tagging/converting, amplifying, or detecting RNA or DNA as described herein.

The term "sample" or "biological sample" refers to any composition containing or presumed to contain nucleic acid. The term includes purified or separated components of cells, tissues, or blood, e.g., DNA, RNA, proteins, cell-free portions, or cell lysates. In the context of the presently disclosed device, the sample is liquid, e.g., blood or a blood component (plasma or serum), urine, semen, saliva, sputum, mucus, semen, tear, lymph, cerebral spinal fluid, mouth/throat rinse, bronchial alveolar lavage, material washed from a swab, etc. Samples also may include constituents and components of in vitro cultures of cells obtained from an individual, including cell lines. The liquid sample can also be partially processed from a sample directly obtained from an individual, e.g., cell lysate or blood depleted of red blood cells.

In the context of the present disclosure, the term "unbound liquid" or "unbound sample" refers to liquid and other components (e.g., proteinaceous material or cell debris) that is not bound to a solid support or MGP, e.g., liquid depleted of nucleic acids or other target. The unbound liquid may still include a residual amount of nucleic acids or target.

A "control" sample or value refers to a value that serves as a reference, usually a known reference, for comparison to a test sample or test conditions. For example, a control can be prepared for reaction conditions. For example, a positive control for the presence of nucleic acid could include primers or probes that will detect a sequence known to be present in the sample (e.g., a housekeeping gene such as beta actin, beta globin, DHFR, or succinate dehydrogenase, or a known added polynucleotide, e.g., having a designated length). An example of a negative control is one free of nucleic acids, or one including primers or probes specific for a sequence that would not be present in the sample, e.g., from a different species. A control can also represent an average value or a range gathered from a number of tests or results. One of skill will understand that the selection of positive and negative control will depend on the particular assay, e.g., so that the control is cell type and organism-appropriate. One of skill in the art will recognize that controls can be designed for assessment of any number of parameters, e.g., protein solubility, nucleic acid stability, nucleic acid yield, etc. Controls are also valuable for determining the significance of data. For example, if values for a given parameter are widely variant in controls, variation in test samples will not be considered as significant.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

III. Samples Containing Nucleic Acids

Samples for nucleic acid amplification can be obtained from any source suspected of containing nucleic acid. In some embodiments, the sample is a liquid sample, e.g., urine, saliva, blood or a blood fraction (e.g. plasma or serum), cell culture, tears, semen, lymph, milk, placental fluid, mucus, and non-animal based liquid. In some embodiments, the sample is gathered on a swab or wipe, e.g., mucosal tissue, buccal sample, vaginal or cervical sample, skin, or sample from an instrument or surface wipe. Samples can be cellular or non-cellular.

In a sample that includes cells, the cells can be separated out (e.g., using size-based filtration or centrifugation), thereby leaving cell free nucleic acids (cfNA), including nucleic acids in exosomes, microvesicles, viral particles, or those circulating freely. Alternatively, the cells can be lysed to obtain cellular nucleic acids, either in the presence of protein-based sample collection matrix or before addition of the cellular lysate to the protein-based sample collection matrix.

IV. Solution for Solubilizing Protein-Based Matrix

The protein-based matrices described herein retain their structure and bind nucleic acid in water and physiologically acceptable liquids, but lose structure and can be solubilized in highly chaotropic solutions. In some embodiments, the chaotrope concentration in solution is 2 M or higher, e.g., about 3-8 M, 3-6 M, 3.5-5.5 M, 3.5-5 M, 3 M, 4 M, 5 M, 6 M, 7 M, or 8 M (e.g., up to limit of solubility). Chaotropes act to disrupt membranes, denature protein and dissociate it from nucleic acids, and to inhibit nuclease activity. Appropriate chaotropes include guanidine thiocyanate, guanidine hydrochloride, guanidine isocyanate, guanidine carbonate, urea, sodium iodide, sodium perchlorate, sodium trichloroacetate, thiourea, and combinations of any number thereof.

The solubilizing solution can include other components such as detergent, reducing agent, chelator, and/or buffer. In some embodiments, the solution comprises a solution about 3-6 M chaotrope, about 0.5-10% detergent, about 25-500 mM reducing agent, and buffer maintaining pH of the solution at about 3.5-8. In some embodiments, the solution comprises about 3.5-5 M chaotrope, 3-5% detergent, 100-150 mM reducing agent, and citrate buffer at a pH 6-6.5, with citrate concentration ranging from 10-500 mM, e.g., 30-200 mM. In some embodiments, the citrate buffer comprises 30 mM sodium citrate and 0.48 mM citric acid.

Appropriate detergents include non-ionic detergents (e.g., polydocanol, Tween 20, Tween 80, Triton X100, Igepal, NP-40) and ionic detergents (e.g., sarcosines, polyoxyethylenesorbitan, sodium dodecyl sulfate (SDS), lithium dodecyl sulfate (LDS), sodium taurodeoxycholate (NaTDC), NaTC, sodium glycocholate (NaGC), sodium deoxycholate (NaDC), sodium cholate, NaABS, N-lauroyl sarcosine (NLS)), salts, and combinations of any number thereof. In some embodiments, the detergent is present in solution at about 0.5-10%, e.g., 2-5%, 3-6%, about 1%, 2%, 3%, 4%, 5%, 6%, 7%, 8%, 9% or 10%.

Reducing agents disrupt disulfide bonds and protein structure, and inactivate nucleases. Appropriate reducing agents include dithiothreitol (DTT), 2-mercaptoethanol, 2-mercaptoethylamine, 2-aminoethanethiol, tris(carboxyethyl) phosphine (TCEP), and combinations of any number thereof. In some embodiments, the reducing agent is present in solution at 25-500 mM, e.g., 50-300 mM, 80-200 mM, 100-150 mM, or about 100 mM, 130 mM, 150 mM, or 2001 mM.

An appropriate buffer can be used to maintain the pH of the solution at about 3.5-8, e.g., about 5-7 or about 6-6.5. Buffers that can be used as described herein include a citrate buffering system, e.g., including citric acid and sodium citrate. Additional appropriate buffers include tris(hydroxymethyl) aminomethane (Tris), 2-(N-morpholino) ethanesulfonic acid (MES), N,N-Bis(2-hydroxyethyl)-2-aminoethanesulfonic Acid (BES), 1,3-bis(tris(hydroxymethyl) methylamino) propane (Bis-Tris), 4-(2-hydroxyethyl)-1-piperazineethanesulfonic acid (HEPES), 3-(N-morpholino) propanesulfonic acid (MOPS), N,N-bis(2-hydroxyethyl) glycine (Bicine), N-[tris(hydroxymethyl)methyl] glycine (Tricine), N-2-acetamido-2-iminodiacetic acid (ADA), N-(2-Acetamido)-2-aminoethanesulfonic acid (ACES), piperazine-1,4-bis(2-ethanesulfonic acid) (PIPES), bicarbonate, phosphate, EDTA, and combinations of any number thereof. Sodium citrate and EDTA can also act as chelators. One of skill in the art will appreciate that the buffer concentration can vary depending on the selection of buffer and sample type, and that the pH can be adjusted using a compatible acid or base.

V. Nucleic Acid Isolation and Detection

Methods for isolating nucleic acids from biological samples are known, e.g., as described in Sambrook, and several kits are commercially available (e.g., DNA Isolation Kit for Cells and Tissues, DNA Isolation Kit for Mammalian Blood, High Pure FFPET DNA Isolation Kit, High Pure RNA Isolation Kit, High Pure Viral Nucleic Acid Kit, and MagNA Pure LC Total Nucleic Acid Isolation Kit, available from Roche). In some embodiments, the nucleic acids and solubilized protein-based matrix as described herein can be used as input for a nucleic acid isolation method such that the nucleic acid is separated from protein and other components.

In some embodiments, the nucleic acid isolation involves use of a filter, e.g., a glass fiber filter, e.g., in a filter tube. In some embodiments, the nucleic acid isolation involves use of a solid or semisolid support, e.g., particle (e.g., microparticles or beads). In either case, the nucleic acids are immobilized on the filter or microparticles, while other components do not bind or bind with lower affinity than the nucleic acids.

In some embodiments, the microparticle is a magnetic glass particle (MGP). MGPs comprise glass that non-covalently binds nucleic acids, and at least one magnetic core (e.g., a dispersion of magnetic cores) that respond to a magnetic field. The glass is not necessarily pure silica, though silica can be a component. MGPs are small enough to be pipetted in a standard pipette tip and form a suspension, typically 0.5-15 um. MGPs are roughly spherical on average, and can be porous or non-porous. The magnetic core can be ferromagnetic or paramagnetic (only magnetized in the presence of a magnetic field). Suitable MGPs are described in more detail, e.g., in U.S. Pat. Nos. 6,255,477 and 6,545,143.

The glass component of either the filter or MGP is typically silica based, e.g., silicon oxide and glass powder, alkylsilica, aluminum silicate, or, NH2-activated silica. In some embodiments, the glass comprises at least one metal oxide (e.g., $SiO_2$, $B_2O_3$, $Al_2O_3$, $K_2O_3$, CaO, and/or ZnO). Nucleic acid binds to glass in chaotropic solution. As indicated above, chaotropic solutions can include guanidinium thiocyanate (GuSCN), guanindine hydrochloride, urea, sodium iodide, sodium perchlorate, thiocyanate ion, iodine ion, perchlorate ion, nitrate ion, bromine ion, acetate ion, chlorine ion, fluorine ion, or sulfur ion, or combinations thereof. In some embodiments, the chaotrope is in solution at about 1-10 M, e.g., 2-8 or 4-6 M, to allow nucleic acid binding.

Wash solutions can be used to remove unbound components, e.g., proteins, salts, etc. The wash solution should retain the nucleic acids bound to the solid support, which can be accomplished, e.g., by using a wash at an acidic pH, or by maintaining the concentration of the chaotrope.

Nucleic acids are typically eluted from any solid support before analysis, though MGPs are compatible with some assays (e.g., detection of a labeled probe hybridized to nucleic acid on the MGP, PCR, or where elution occurs as part of the assay, such as Southern blotting). Elution buffers interfere with the non-covalent (e.g., associative or ionic) interaction of nucleic acid with the MGP, e.g., water, buffer with pH>7 or lower chaotropic concentration or ionic strength than used for binding nucleic acids to the MGPs, and/or elevated temperature, as will be appreciated by one of skill in the art.

The purified nucleic acid sample can be used for detection, e.g., using next generation sequencing, microarray (RNA or DNA), Southern or Northern Blot, or nucleic acid amplification, e.g., using any primer-dependent method. DNA-based methods can be used for amplification and detection, e.g., PCR. In some embodiments, real time or quantitative PCR is used (RTPCR or qPCR). qPCR allows for reliable detection and measurement of products generated during each cycle of PCR process. Such techniques are well known in the art, and kits and reagents are commercially available, e.g., from Roche Molecular Systems, Life Technologies, Bio-Rad, etc. See, e.g., Pfaffl (2010) *Methods: The ongoing evolution of qPCR* vol. 50; *PCR Strategies* (Innis et al., 1995, Academic Press, San Diego, Calif.) at Chapter 14; *PCR Protocols: A Guide to Methods and Applications* (Innis et al., Academic Press, N Y, 1990).

In some embodiments, a preliminary reverse transcription step is carried out to prepare cDNA complementary to RNA in the sample (also referred to as RT-PCR, not to be confused with real time PCR). The cDNA can then be used as a template for PCR. See, e.g., Hierro et al. (2006) 72:7148. The term "qRT-PCR" as used herein refers to reverse transcription followed by quantitative PCR. Both reactions can be carried out in a single tube without interruption, e.g., to add reagents. For example, a polyT primer can be used to reverse transcribe all mRNAs in a sample with a polyA tail, or a primer can be designed that is specific for a particular target transcript that will be reverse transcribed into cDNA. Additional RNA-based methods of amplification can also be used, e.g., nucleic acid sequence based amplification (NASBA) or transcription mediated amplification (TMA).

Detection devices are known in the art and can be selected as appropriate for the selected labels. Detection devices appropriate for quantitative PCR include the cobas and Light Cycler systems (Roche), PRISM 7000 and 7300 real-time PCR systems (Applied Biosystems), etc.

VI. Kits

In some embodiments, reagents and materials for carrying out the presently disclosed methods are included in a kit.

In some embodiments, the kit for capturing nucleic acids comprises a protein-based matrix. In some embodiments, the protein-based matrix is formed into a strip, swab, or wipe. In some embodiments, the protein-based matrix consists essentially of a protein selected from silk, collagen, keratin, albumin, and milk protein. In some embodiments, the protein-based matrix is a combination of two or more proteins selected from silk, collagen, keratin, albumin, and milk protein. In some embodiments, the protein based matrix is sterilized and sealed. In some embodiments, the protein-based matrix is formed into a strip, and is enclosed in a non-protein cover (e.g., paper, cardboard, plastic, etc.) with an area exposed to add sample.

In some embodiments, the kit further includes a solution comprising about 3-6 M chaotrope, about 0.5-10% detergent, about 50-500 mM reducing agent, and buffer maintaining pH of the solution at about 3.5-8 or 5-8. In some embodiments, the solution comprises 3.5-5.5M guanidinium salt. In some embodiments, the solution comprises 3-5% detergent, e.g., non-ionic detergent. In some embodiments, the solution comprises 100-150 mM reducing agent. In some embodiments, the solution comprises a buffer (e.g., citrate buffer) at pH 6-7. In some embodiments, the solution comprises a chelator. In some embodiments, the solution is provided in concentrated form (e.g., 5× or 10×), and when diluted, has the concentrations listed above.

In some embodiments, the kit further comprises components for isolating the nucleic acids from solubilized protein. In some embodiments, such components include magnetic glass particles (MGPs) or microbeads. In some embodiments, such components include filter tubes. In some embodiments, such components further include wash buffer and/or elution buffer. In some embodiments, the wash buffer and/or elution buffer is provided in concentrated form and is diluted before use.

In some embodiments, the kit further includes at least one control, e.g., a protein-based matrix holding nucleic acid fragments of known size and concentration. In some embodiments, the kit further includes consumables, e.g., plates or tubes for nucleic acid capture and/or separation, tubes for sample collection, etc. In some embodiments, the kit includes containers for storing the protein-based matrix before processing/solubilizing. In some embodiments, the kit further includes instructions for use, reference to a website, or software.

VII. Example

Example 1: Assessment of Silk as a Protein-Based Sample Collection Matrix

Silk fabric was purchased from Jo Ann Fabrics and cut into small strips. A strip was added to each of three test tubes (FIG. 1). Three different buffers were tested for the ability to solubilize the silk, thus allowing it to be pipetted and processed for downstream nucleic acid isolation.

Tube 1 contained 1 mL buffer (4 M Guanidinium thiocyanate, 30 mM sodium citrate, 129.6 mM dithiothreitol (DTT), 4% polydocanol, 0.48 mM citric acid, pH 6.2). Tube 2 contained 0.5 mL Proteinase K solution (10 mM Tris-HCL pH, 1 mM EDTA, 5 mM CaCl2, 5 mM Ca-EDTA, 50% glycerin, 1 mg/ml proteinase K) Tube 3 contained 0.5 mL buffer and 0.5 ml. Proteinase K solution.

The tubes were incubated at 55 C for 30 minutes, cooled, and photographed.

Figure 2:
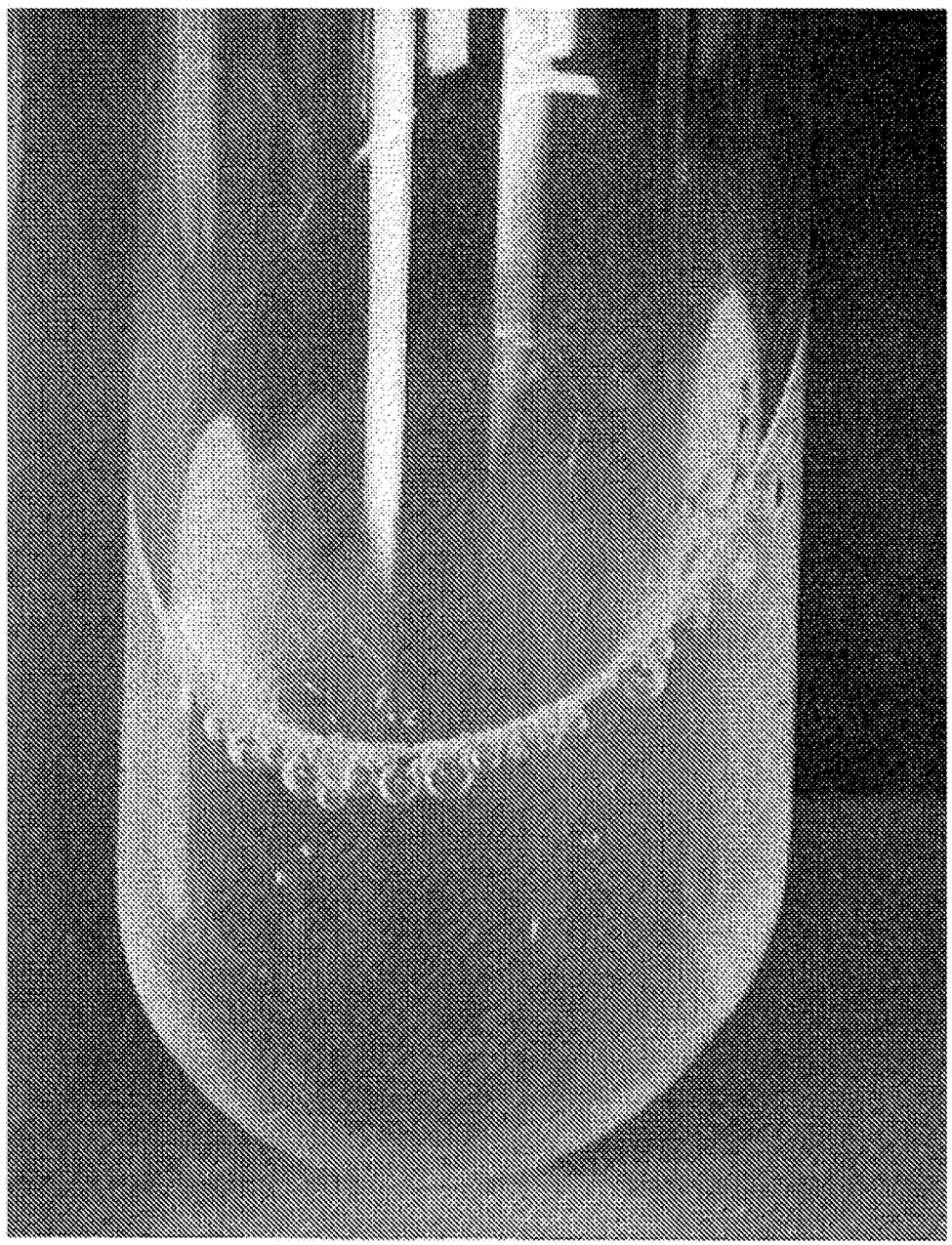
FIG. 2 shows the effect of chaotropic solution (4 M guanidine thiocyanate) on the protein-based matrix.
Figure 3:
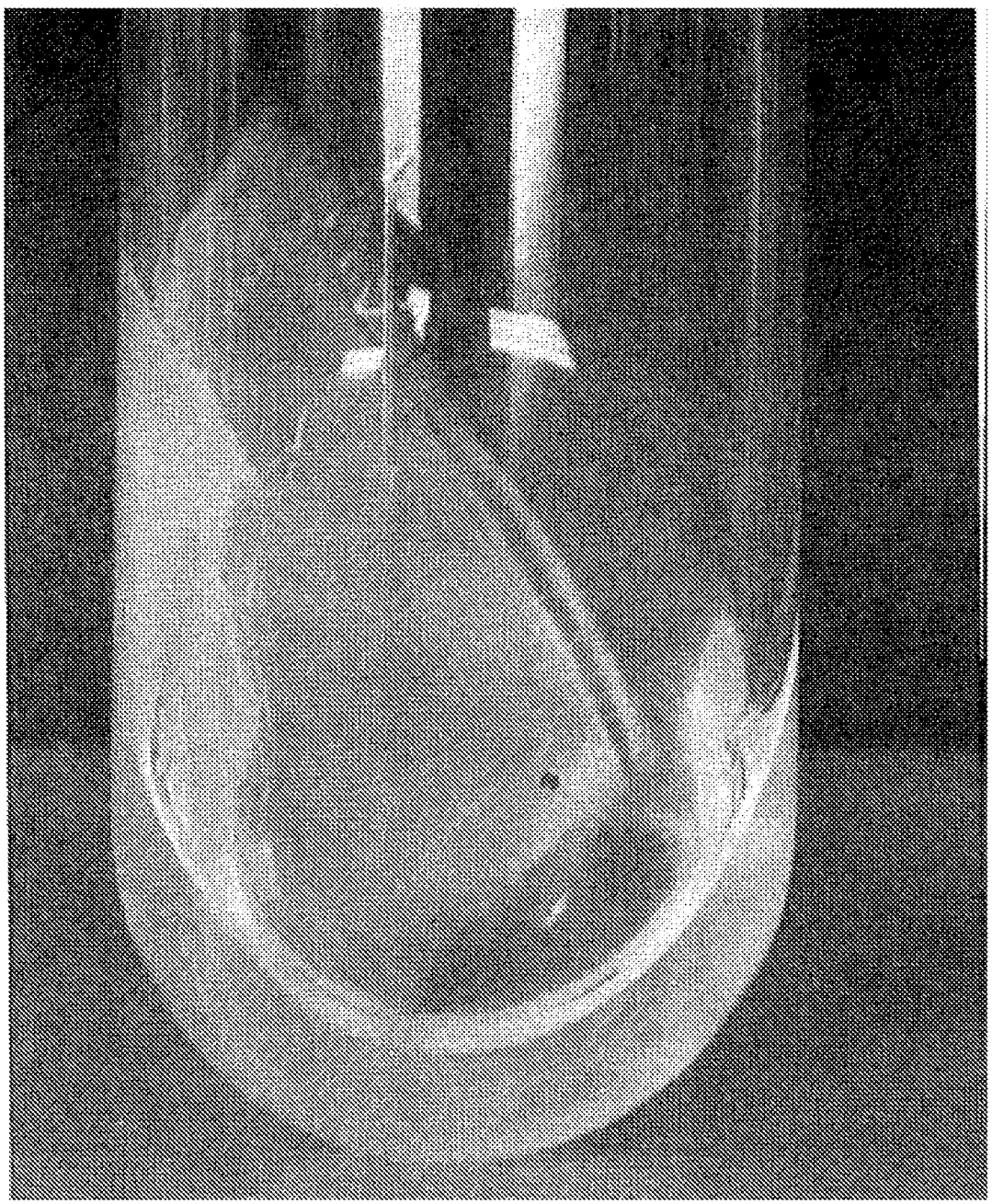
FIG. 3 shows the effect of proteinase K solution on the protein-based matrix.
Figure 4:
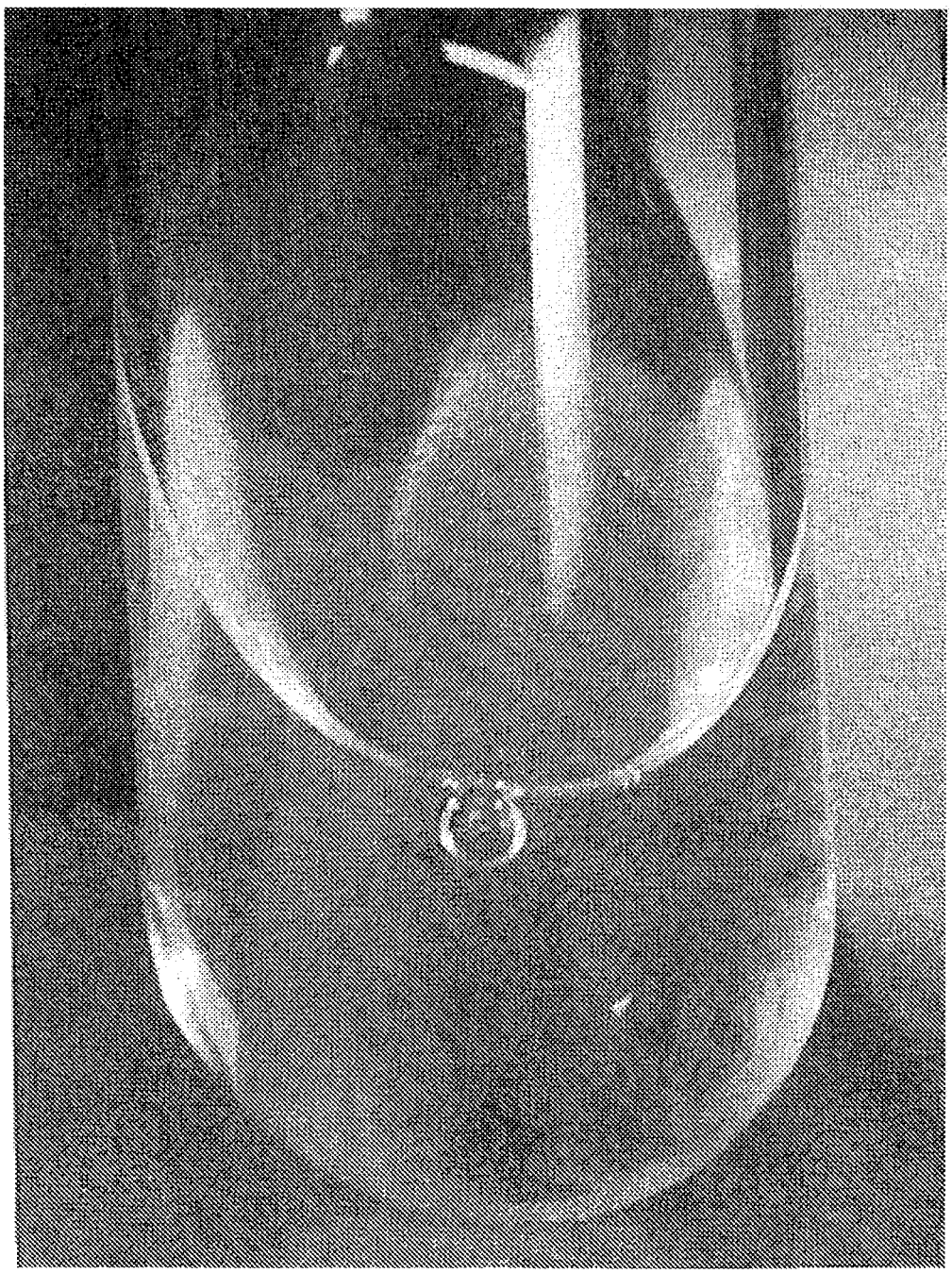
FIG. 4 shows the effect of a 50-50 mix of chaotropic solution and proteinase K (final concentration 2 M guanidine thiocyanate).

As shown in FIG. 2, the silk was significantly disrupted with loss of integrity in the woven fabric in Tube 1. There were minimal fibers visible in suspension. FIG. 3 shows that Proteinase K had no detectable effect in Tube 2. FIG. 4 shows that the combined buffers resulted in some disruption of the silk fabric.

The results indicate that a protein-based matrix can be used for sample collection and effectively solubilized in chaotropic buffer.

Example 3: Use of Protein-Based Matrix in Swabs

Swabs are used extensively in both molecular diagnostics and molecular forensic applications. The swabs are used to physically retain biological samples from surfaces, including human skin in the case of MRSA or CT/NG testing, or inert surfaces in the case of the sampling of a crime scene for subsequent human identity testing. Swabs are typically made from spun or woven, fibrous, cellulosic compositions supported on a polymeric cylindrical plastic core, and as such they do not dissolve in conventional sample preparation liquids including Guanidinium Thiocyanate. A swab produced with the fibrous material made from spun or woven proteinaceous materials, such as silk, still has all the desirable properties of a cellulosic swab head as far as its ability to sample biological samples from skin or inert surfaces. The swab can collect and preserve biological samples for downstream molecular analyses.

Such a swab can efficiently collect biological material from a surface, and the subsequent analysis is enhanced through the increased efficiency of extraction and recovery of the biological material from the proteinaceous swab when suspended in an extraction liquid. The efficiency of extraction and recovery of a biological sample from a conventional swab is never complete, due to the volume of the extraction liquid which is retained within and around the swab head.

The protein-based (e.g., silk) swab head can dissolve leaving a solid core. Alternatively, the solid core can be constructed from a similar proteinaceous material so that the whole swab can be dissolved and allow for transfer of the suspended biological sample without mechanical interference by the solid core with, for example, a transfer pipette.

Example 4: Use of Protein-Based Matrix in a Woven Fabric

The concept can be extended beyond swabs to other formats, including woven substrates, such as fabrics. A woven silk fabric pad can capture and release biological samples analogously to the swab head described above. They could be configured in many forms, including filters, as are used in air sampling. Such a soluble filter material provides access to a greater amount of the captured biological materials when treated with the chaotropic salt. This can be used for air monitoring for biowarfare agents, for example.

While the invention has been described in detail with reference to specific examples, it will be apparent to one skilled in the art that various modifications can be made within the scope of this invention. Thus the scope of the invention should not be limited by the examples described herein. All patents, publications, websites, Genbank (or other database) entries disclosed herein are incorporated by reference in their entireties.

I claim:

1. A kit for isolating nucleic acids from a sample, the kit comprising:
   a) a protein-based matrix configured to collect sample; and b) a solution comprising about 3-6 M chaotrope, about 4% detergent, 80-200 mM reducing agent, and buffer maintaining pH of the solution at about 6-6.5.

2. The kit of claim 1, wherein the protein-based matrix forms a swab.

3. The kit of claim 1, wherein the protein-based matrix forms a strip to collect liquid sample.

4. The kit of claim 1, further comprising processing vessels.

5. The kit of claim 1, further comprising filter tubes or magnetic glass beads (MGPs).

6. The kit of claim 5, further comprising wash buffer and elution buffer.

7. The kit of claim 1, wherein the protein-based matrix is silk.

8. The kit of claim 1, wherein the chaotrope is guanidinium salt.

9. The kit of claim 1, wherein the detergent is a non-ionic detergent.

10. The kit of claim 1, wherein the reducing agent is dithiothreitol.

11. The kit of claim 1, wherein the buffer is a citrate buffer.

12. The kit of claim 1, wherein the pH of the solution is 6-7.

13. The kit of claim 1, further comprising a container for storing the protein-based matrix and sample.

* * * * *